United States Patent
Whitehurst et al.

(10) Patent No.: US 8,048,189 B2
(45) Date of Patent: Nov. 1, 2011

(54) BUFFERED AMINO ALCOHOL SOLUTIONS OF N-(N-BUTYL)THIOPHOSPHORIC TRIAMIDE (NBPT) AND UREA FERTILIZERS USING SUCH SOLUTIONS AS UREASE INHIBITORS

(75) Inventors: Garnett B. Whitehurst, New Bern, NC (US); Brooks M. Whitehurst, New Bern, NC (US)

(73) Assignee: Whitehurst Associates Inc., New Bern, NC (US)

( * ) Notice: Subject to any disclaimer, the term of this patent is extended or adjusted under 35 U.S.C. 154(b) by 357 days.

(21) Appl. No.: 12/378,493

(22) Filed: Feb. 17, 2009

(65) Prior Publication Data

US 2010/0206030 A1    Aug. 19, 2010

(51) Int. Cl.
- C05D 9/02 (2006.01)
- C05F 11/00 (2006.01)
- A01N 25/00 (2006.01)
- C07F 9/22 (2006.01)
- C07F 9/28 (2006.01)

(52) U.S. Cl. .......... 71/11; 71/1; 71/27; 71/64.1; 71/902; 564/12

(58) Field of Classification Search ............ 71/1, 11, 71/27–64.13, 902; 252/380, 364; 564/12–15, 564/153
See application file for complete search history.

(56) References Cited

U.S. PATENT DOCUMENTS

| | | |
|---|---|---|
| 3,152,039 A | 10/1964 | Mattson |
| 3,353,949 A | 11/1967 | Nau |
| 4,530,714 A | 7/1985 | Kolo et al. |
| 5,024,689 A | 6/1991 | Sutton et al. |
| 5,352,265 A | 10/1994 | Weston et al. |
| 5,364,438 A | 11/1994 | Weston et al. |
| 5,698,003 A | 12/1997 | Omilinsky et al. |
| 6,830,603 B2 | 12/2004 | Whitehurst et al. |
| 6,852,904 B2 * | 2/2005 | Sun et al. ............. 604/359 |
| 2004/0163434 A1 | 8/2004 | Quin |
| 2006/0185411 A1 | 8/2006 | Hojjatie et al. |
| 2007/0077428 A1 * | 4/2007 | Hamed et al. ............. 428/393 |
| 2007/0157689 A1 | 7/2007 | Sutton et al. |
| 2007/0295047 A1 | 12/2007 | Sutton et al. |
| 2010/0206030 A1 * | 8/2010 | Whitehurst et al. ............. 71/30 |
| 2010/0206031 A1 * | 8/2010 | Whitehurst et al. ............. 71/30 |

FOREIGN PATENT DOCUMENTS

WO    WO 2008/000196    1/2008

* cited by examiner

*Primary Examiner* — Jerry A Lorengo
*Assistant Examiner* — Jennifer Smith
(74) *Attorney, Agent, or Firm* — MacCord Mason PLLC

(57) ABSTRACT

Reduced volatility of urea fertilizers are prepared in accordance with the present invention by first preparing an N-(n-butyl)-thiophosphoric triamide (NBPT) solution by dissolving NBPT in a mixture of an amino alcohol having the formula 1—$(H)_x$—N—$((CH_2)_m$—OH$)_n$ where m is 1-3, x is 0 or 1, and n is 2 when x is 1 and 3 when x is 0: or the formula 2—$(H)_y$—N—$((CH_2)$—CHOH—$CH_3)_z$ such that the length of the carbon chain where the secondary hydroxyl group is located is 3, y is 0 or 1, and z is 2 when y is 1 and 3 when y is 0, and a carboxylic acid having 6 or fewer carbon atoms. The solution is then combining with a urea fertilizer in granular or liquid form.

18 Claims, No Drawings

BUFFERED AMINO ALCOHOL SOLUTIONS OF N-(N-BUTYL)THIOPHOSPHORIC TRIAMIDE (NBPT) AND UREA FERTILIZERS USING SUCH SOLUTIONS AS UREASE INHIBITORS

BACKGROUND OF THE INVENTION (1) Field of the Invention

Fertilizer materials derived primarily from urea with other additional useful additives and plant nutrient materials are treated with a buffered solution of N-(n-butyl) thiophosphoric triamide (NBPT) dissolved in a mixture of one or more amino alcohols with one or more carboxylic acids having 6 or fewer carbon atoms to reduce nitrogen volatilization. The solution may be applied as a coating for granular urea fertilizers, or mixed with an aqueous fertilizer solution.

(2) Description of the Prior Art

The degradation of urea to release ammonia when applied to the soil is well known. The losses of applied nitrogen due to volatilization can be substantial (see review by Terman "Volatilization Losses of Nitrogen as Ammonia from Surface Applied Fertilizers, Organic Amendments and Crop Residues" in Advances in Agronomy 31: 189-223, 1979). The losses of nitrogen from urea applied to the soil are dependent upon a number of factors including: soil pH, soil temperature, soil moisture, cation exchange capacity of the soil and soil organic matter content. Greater losses of nitrogen from urea are observed as the soil temperature increases, as the soil pH increases and as the organic matter content increases. Decreased nitrogen losses of nitrogen from urea are observed whenever the soil moisture is high. In addition the depth of fertilizer placement influences nitrogen losses and surface placements are generally subject to greater nitrogen loss. The relative humidity at time of fertilization can influence losses. Recent rainfall events will tend to reduce losses if sufficient water is present to distribute the fertilizer into the soil.

Methods for controlling volatile nitrogen loses from urea have included the application of metal salts of copper and zinc, boron compounds, organic urease inhibitors, acid coatings, polymer coatings, and reaction of urea with aldehydes to form a slow release molecular adduct (see background in Whitehurst. et. al. U.S. Pat. No. 6,830,603 which is incorporated by reference). A number of extended release products have been proposed to help control volatile nitrogen losses.

N-(n-butyl)-thiopsosphoric triamide (NBPT) is a known urease inhibitor described by (Kolc et. al. U.S. Pat. No. 4,530,714). The compound is a waxy solid with poor water solubility making it difficult to coat urea and achieve adhesion of the compound. The compound undergoes hydrolysis and is thermally unstable.

The 714 patent describes the mixing of NBPT with organic solvents (acetone, disobutylketone, methanol, ethanol, 2-propanol, ether(diethyl), tolune, methylene chloride) to distribute the compound into the soil in an effective concentration range which can be anywhere from 5 ppm to 100 ppm depending upon the soil. The organic solvents described by the 714 patent are either too flammable for use or pose significant health risks to be considered suitable for coating urea granules.

In an alternate method, the 714 patent indicates that NBPT can be mixed with solids such as gypsum or clay to distribute the compound into the soil in an effective concentration.

Omilinsky et. al. (U.S. Pat. No. 5,698,003) describes the dissolution of NBPT with a glycol such as propylene glycol or ethylene glycol and esters of glycols. Glycols are compounds with adjacent alcohol groups in the chemical structure. The dissolution may contain a co-solvent liquid amide such as N-methyl-2-pyrrolidine and potentially a surfactant or dispersing agent such as polyethylene glycol or esters of polyethylene glycol (polyether alcohols). The patent indicates that esters of glycerol (a triol) may be used as the base solvent. Urea granules containing NBPT are prepared by mixing the urea granules with the NBPT dissolution solvent. Omilinsky et. al. teach that a drying agent such as clay or gypsum may be added to the compositions in the event that a product with excessive wetness is obtained.

Weston et. al (U.S. Pat. No. 5,352,265 and U.S. Pat. No. 5,364,438) teach the dissolution of NBPT in liquid amides such as 2-pyrrolidone or N-alkyl-2-pyrrolidones such as N-methyl-2-pyrrolidone to prepare both solid urea formulations (265 patent) or liquid formulations (438 patent).

Hojjatie et. al. (US 2006/0185411) teach the use of a number of sulfur salts of calcium or magnesium (calcium polysulfide, thiosulfate, magnesium thiosulfate) as urease inhibitors to prepare granular or liquid urea compositions.

Quin (US 2004/0163434) teaches the formation of a sulfur coated urea which may contain the urease inhibitor NBPT supplied from a proprietary liquid formulation sold as Agrotain® and distributed by Agrotain International LLC, Indiana, USA.

Sutton et. al. (U.S. Pat. No. 5,0247,689) teach the formation of a liquid fertilizer that includes urease inhibitors such as NBPT and nitrification inhibitors such as dicyandiamide in aqueous mixtures of urea ammonium polyphosphate, ammonium thiosulfate and potentially other plant growth improving compounds.

Sutton (US 2007/0295047) teaches the formation of a solid fertilizer comprised of urea and a urea-formaldehyde polymer which may additionally include a urease inhibitor such as NBPT.

Sutton et. al. (US 2007/0157689) describes a fertilizer additive composed of urea, a urea-formaldehyde polymer and NBPT dissolved in an N-alkyl-2-pyrrolidone.

Urea is a high nitrogen analysis material which is often desirable as a starting material for making additional fertilizer products providing phosphorus or potassium as primary nutrients, calcium, magnesium or sulfur as secondary nutrients or micronutrients such as boron, copper, iron, manganese, molybdenum and zinc.

Whitehurst et. al. (603 patent) describe a coating methodology wherein a boron containing urease inhibitor composition may be used to add additional nutrients such as phosphate, potassium, etc. The coating of urea with other materials is known and the references in Whitehurst et. al. (603 patent) provides a partial summary of prior art in the area. The inhibitors and binders of this invention are aqueous mixtures that include ethanolamine borates, diethanolamine borates or triethanolamine borates and mixtures of these.

Commercial products containing aqueous ethanolamine borates or triethanolamine borates are distributed under the trade name of ARBORITE® by Encee Chemical Sales, North Carolina, USA. The product is further identified by a binder number for separation of the different mixtures available.

SUMMARY OF THE INVENTION

Generally, reduced volatility urea fertilizers are prepared in accordance with the present invention by first preparing an N-(n-butyl)-thiophosphoric triamide (NBPT) solution by dissolving NBPT in a mixture of an amino alcohol having the formula 1—$(H)_x$—N—$((CH_2)_m$—$OH)_n$ where m is 1-3, x is 0 or 1, and n is 2 when x is 1 and 3 when x is 0: or the formula 2—$(H)_y$—N—$((CH_2)$—CHOH—$CH_3)_z$ such that the length of the carbon chain where the secondary hydroxyl group is located is 3, y is 0 or 1, and z is 2 when y is 1 and 3 when y is 0, and a carboxylic acid having 6 or fewer carbon atoms. The solution is then combined with a urea fertilizer in granular or liquid form.

As used herein, the term "urea fertilizer" encompasses urea and mixtures of urea with other primary nutrients, secondary nutrients and/or micronutrients. Preferably, urea comprises at least 40% by weight of the urea fertilizer. Unless otherwise noted all percentages refer to weight percentages or parts per 100 parts. NBPT—N-(n-butylthiophosphoric triamide) is an item of commerce and is sold in various forms which may contain impurities.

The amino alcohols required to practice the invention are those compounds which possess a primary, secondary or tertiary amine function with an alcohol functional group on an adjacent carbon to the nitrogen atom. The compounds will further have a $pK_a$ of between about 7.5 and 10. The following amino alcohols (alkanolamines) needed to practice the invention are items of commerce:

MEA—ethanolamine
DEA—diethanolamine
TEA—triethanolamine
MIPA—monoisopropanolamine
DIPA—diisopropanolamine The above materials are items of commerce and except for DIPA occur as liquids at room temperature. TEA and DEA may be obtained as mixtures which include MEA. DIPA may be obtained as mixture with MIPA.

The acids needed to practice the invention may be described as carboxylic acids with 6 or fewer carbon atoms with or without hydroxyl groups. The acids required to practice the invention should have pKa's of approximately 5 or less.

Acetic acid, propionic acid butyric, valeric and caproic acid are items of commerce. These acids may be obtained as a substantially pure materials or with small amount of water <10%. The acids may additionally have an alcohol group such as lactic acid (2-hydroxypropionic acid) which is an item of commerce. Other examples of hydroxyacids include the hydroxybutyric acids (2-hydroxy, 3-hydroxy, or 4 hydroxybutanoic acids).

The term solubility limit as used below refers to the measurement of maximum amount of NBPT which will dissolve in a buffered mixture prepared from the amino alcohols. To determine the solubility limit a mixture is prepared by melting NBPT into a weighed amount of the buffered liquid mixture of the invention at the desired concentration of NBPT. The resulting mixture is observed over a period of time to assess whether solids form upon standing. If solids form upon standing the mixture is deemed unstable and the solubility limit is considered exceeded.

All solubility limits are expressed in weight percentages and are understood to imply the limit of the solubility of NBPT.

Additionally, the practice of the invention may include other items of commerce including ethylene glycol and propylene glycol. The glycols can be used as co-solvents or as agents to reduce viscosity of various mixtures to control spreadability of a formulation.

The production of some coated products may include one or more sources of additional plant nutrients as water soluble salts such as potassium chloride, potassium sulfate, and salts of iron, copper, zinc, manganese, and others; and partially water soluble salts such as gypsum, potassium magnesium sulfate and others commonly employed in agricultural practice. The only requirement for the selection of the additional plant nutrient source is that if be compatible with urea. Compatibility of many fertilizer materials can be determined from the "Farm Chemicals Handbook" published by Meister Publishing Co. Ohio, USA.

To make mixed fertilizer compositions using the invention, one or more materials providing plant nutrients other than urea is preferably used in a powdered form. The term powder for purposes of the invention shall mean any finely divided substance prepared by some dry grinding process. There are numerous forms of dry grinding equipment available including hammer mills or pin mills, etc. A powder for purposes of the invention shall imply any finely divided material with a particle size less than 0.300 mm (300 µm).

Mixed fertilizer compositions are described by expressing the weight percentage of the primary elements present in the following manner: XX-YY-ZZ; where XX is the percentage of nitrogen, YY is the phosphate percentage expressed as $P_2O_5$, and ZZ is the potassium content expressed as the percentage $K_2O$. When secondary elements are present the percentages are often listed after the primary elements in the order calcium, magnesium and sulfur or by stating the analysis for the secondary element followed by the symbol for the element. For example a 35-9-0-2Ca-2Mg,-3S would indicate a material (fertilizer) with 35% nitrogen, 9% $P_2O_5$, 0% $K_2O$, 2% Ca, 2% Mg and 3% S.

DETAILED DESCRIPTION OF THE INVENTION

To practice the invention, a buffered mixture is prepared from an amino alcohol identified above by reaction of the amino alcohol with an acid selected from the short chain carboxylic acids which have pKa's of 5 or less. The reaction is carried out by mixing the amino alcohol with a quantity of acid such that the pH of the resulting mixture lies between 8 and 10. The best performance is obtained whenever the pH of the buffered mixture lies between 9 and 10.

The reaction of the amino alcohol with an acid forms the ammonium ion form of the amine and the neutralized acid becomes a carboxylate ion. Depending upon the $pK_a$ of the amino alcohol, the mixture resulting from the reaction will contain the amino alcohol (alkanolamine), an alkanolammoium ion, a carboxylate ion and water. The water is formed as a product of the neutralization reaction.

The reaction is exothermic and may require cooling. If the temperature of the buffered mixture is above 60° C. it must be cooled before proceeding with the NBPT dissolution step.

Following preparation of the buffered mixture, NBPT is dissolved in the buffered mixture to prepare urea containing compositions that include this valuable urease inhibitor. The dissolution step for NBPT is preferably carried out by the melting of the solid NBPT into the buffered mixture. A temperature of 50° C. to 60° C. may be used to help melt NBPT into the buffered mixture in mixing equipment which avoids excessive aeration. The melting step may be accomplished using jacketed vessels or heating coils provided that the melt is swept away from the heat source by stirring the mixture as it forms using an agitator or circulation pump to prevent a localized hot spot from forming. The melting step is preferably performed using hot water to avoid thermal damage to the NBPT. Steam may be used; however, both rapid circulation while mixing and temperature controls should be employed to reduce thermal degradation of NBPT.

In the preferred embodiment of the invention; a buffered NBPT containing mixture is formed by mixing NBPT with a buffered mixture as defined above sufficient to give a concentration from 2% NBPT to 40% NBPT by weight depending upon the solubility of limit of NBPT in the buffered mixture.

To assist in the formulation processes described below, a dye or colorant can be added to the buffered mixture containing mixture. Any commonly used colorant including food dyes may be added to the mixture to provide visual evidence of the uniformity of the distribution of the buffered mixture containing NBPT as described below. Methylene blue is a commercially available blue colored substance which could be dissolved in water or alcohol to add to the buffered NBPT containing mixture.

Once NBPT is dissolved the buffered mixture with or without a colorant, useful compositions can be obtained by contacting granular urea with the NBPT present. Coated granular urea containing products with from 0.050% to 0.25% NBPT can be made which have applications in agriculture or forestry where nitrogen fertilization is needed.

The amount of urease inhibitor (NBPT) needed in given coated urea formulation often depends upon the soil type and soil pH and the amount of urease activity due to soil bacteria. The quantity of urease inhibitor needed in the final granular product treated with the buffered mixture containing NBPT could be determined by measuring the urease activity in a range of soils and then determining the amount of inhibitor needed to inhibit that amount of urease in the specific soil where the coated products will be applied. The alternative method involves assessing the volatile nitrogen losses from a range of soils and formulating to achieve a desired amount of control of the volatile nitrogen loss in the specific soil where the coated products will be applied. The practices for measuring urease inhibition or volatile nitrogen losses are described in the patents or literature referenced above.

The coating of granular urea with NBPT dissolved in a buffered mixture of the invention may be accomplished using any commercially available equipment in which a granular product may be comingled with a liquid. The equipment may permit the buffered mixture liquid containing NBPT to be sprayed onto the granules as they tumble in the mixer or the buffered mixture liquid containing NBPT may be dribbled into the granules as they tumble within the mixing equipment. The surface wetted granules from addition of the buffered mixture containing NBPT are then tumbled until the material has been uniformly distributed across the surface of the granules. The resulting NBPT treated urea product may then be stored or packaged as required. A flowability aid or desiccant such as gypsum, silica, monoammonium phosphate, potassium sulfate, potassium magnesium sulfate or clay may be required to ensure flowability of the resulting coated granular product if there is inadequate control of the volume of NBPT containing buffered mixture liquid applied to the coating. Preferably, the buffered mixture liquid containing NBPT is introduced into the mixing equipment via a metering system able to provide reproducible formulations.

The product may be applied to land to provide nitrogen needed by plants to the soil which contain the valuable urease inhibitor NBPT. The granular product materials containing NBPT may be applied using any routinely used application method such as broadcast by ground or aerial spreading equipment, banding using ground application equipment and spotting techniques wherein the fertilizer is placed next to the plant either above ground or in a depression made into the soil surface next to the plant where application is desired.

Another useful set of urea containing formulations may be obtained by adding the buffered mixture containing NBPT to aqueous solutions which contain urea. Commercially available UAN solution a mixture of urea and ammonium nitrate that may contain from about 28% N to 32% N can be mixed with the buffered mixture containing NBPT. The mixing of the NBPT containing buffered mixture with the UAN solution may be accomplished in any commonly used mixing equipment. Once the NBPT containing buffered mixture mixture with UAN is prepared, it may be applied to the soil as conventionally practiced for UAN solution without the NBPT containing buffered mixture.

Another useful set of granular products may be prepared by diluting the NBPT containing buffered mixture with another liquid which may be an aqueous mixture. The resulting diluted NBPT containing mixture can then be used to cause powdered plant nutrient supplying materials to adhere to granular urea. Dilution of the NBPT present in the buffered mixture may be required to avoid using an excessive amount of NBPT in the resulting coated granular products to avoid potential phytotoxicity.

To prepare the diluted NBPT containing mixture the buffered mixture containing NBPT can be measured into the diluting material on a weight or volumetric basis. Any order of addition of the ingredients may be used. The maximum amount of NBPT is limited by solubility limit for NBPT in the diluted mixture or aqueous solubility limit of NBPT in the diluted mixture being prepared.

The mixing of the two materials may be accomplished by any commonly used method: for example; simply tank mixing the two materials prior to use, using a metering system to inject both materials simultaneously, or mixing via a spray injection system if the binder was normally sprayed onto a granular bed to prepare coated urea products.

Coated granular urea products containing additional plant nutrients are then prepared from granular urea, a source or sources of the additional nutrients in powdered form and the diluted NBPT containing mixture described above. Granular urea is first dampened with the diluted buffered NBPT containing mixture followed by mixing to distribute the NBPT containing liquid mixture over the granular urea surface using any commonly used equipment to comingle a liquid with a granular solid. After distribution of the diluted buffered NBPT containing mixture over the granular surface, the additional nutrients in powdered form are added to the dampened mixture and the resulting combined ingredients are further mixed to distribute the powdered materials. In an alternate approach the powdered materials may be first mixed with the granular urea and then the buffered NBPT containing diluted mixture is sprayed onto a tumbling bed of the dry ingredients to agglomerate the dry materials. This later method is particularly suited to continuous processing.

As an embodiment of the invention, a buffered mixture is prepared from MEA and acetic acid with a pH from 8.5-9.5 and then, NBPT is dissolved by melting the compound with sufficient buffered mixture to give about 15% by weight of NBPT. The resulting buffered NBPT containing mixture can be used to treat urea as described above.

As another embodiment of the invention, a buffered mixture is prepared from TEA and acetic acid with a pH of 8.5-9.5 and then NBPT is dissolved by melting the compound with sufficient buffered mixture to give a concentration of 30% NBPT. The resulting buffered NBPT containing mixture can be used to treat urea as described above.

As another embodiment of the invention, a buffered mixture is prepared from MIPA and acetic acid with a pH of 8.5-9.5 and then NBPT is dissolved by melting the compound with sufficient buffered mixture to give a concentration of 25% NBPT. The resulting buffered NBPT containing can be used to treat urea as described above.

As another embodiment of the invention, a buffered mixture is prepared from DIPA and acetic acid with a pH of about 9 and then NBPT is dissolved by melting the compound with sufficient buffered mixture to give a concentration of NBPT up to the solubility limit. The resulting buffered NBPT containing mixture can be used to treat urea as described above.

As another embodiment of the invention, any of the NBPT containing buffered mixtures prepared according to the invention may be diluted by adding a co-diluent such as ethylene glycol or propylene glycol to reduce the viscosity of the buffered NBPT containing mixture.

In another embodiment of the invention, commercially available mixtures of MEA, DEA and TEA may be used to prepare a buffered mixture by reaction of the mixture of amino alcohols with acetic acid to reach a pH of about 9. The resulting buffered mixture is used to dissolve NBPT up to the solubility limit by melting the compound into the buffered mixture. The NBPT containing buffered mixture may be used to treat urea as described above.

In another embodiment of the invention, a buffered solution prepared as described above containing up to about 3.0% by weight NBPT can be dissolved in the triethanolamine borate mixture such as ARBORITE® Binder 78. The resulting mixture could then be used to prepare coated urea granules with both NBPT and a boron compound present as described above.

As another embodiment of the invention, a mixture containing up to about 2% NBPT can be prepared by first making a buffered mixture of triethanolamine and acetic acid as indicated above and then dissolving up to about 20% NBPT in the buffered mixture as described above then mixing the solution (buffered solution containing NBPT) with UAN solution to give a final concentration of NBPT of about 3%. Preferably the concentration of NBPT in the UAN solution would range from about 0.05% to about 0.25% by weight. The liquid formulation may then used directly as a fertilizer solution.

In another embodiment of the invention, a solution containing up to about 15% NBPT dissolved in a buffered mixture of triethanolamine and acetic acid with a pH from 8.5 to 9.5 may be diluted with ARBORITE® Binder 75 to prepare a solution which contains both boron and NBPT. The resulting diluted NBPT solution may then be used to prepare coated urea granules with NBPT, boron and optionally other plant nutrients as indicated above.

When the diluent liquid contains an aqueous ethanolamine borate such as ARBORITE® Binder 75, a secondary or tertiary amino alcohol may be needed to stabilize the mixture. The secondary or tertiary amino alcohol concentration should be kept above about 12% and preferably above about 20% in the final diluted mixture. Below a 12% concentration of the secondary or tertiary amino alcohol in an ethanolamine borate solution a suspension of NBPT in the aqueous mixture may form which requires constant agitation to be used to prepare other products.

EXAMPLES

The following examples are provided to illustrate the practice of the invention. The examples are not intended to illustrate the complete range of compositions possible.

The following abbreviations are employed: MEA (ethanolamine), TEA (triethanolamine), MIPA (monoisopropanolamine or 1-amino-2-propanol) and NBPT (N-n-butylthiophosphoric triamide) UAN (urea ammonium nitrate solution). The term powdered when used is understood to refer to any finely divided material with a particle size less than 250 μm (60 mesh).

In many of the following examples the term melted is used to describe the process of dissolving NBPT into a buffered solvent system. The term melted within this context refers to the heating of the mixture of NBPT and the coating solvent to dissolve the NBPT into the coating solvent. The dissolution step requires a temperature of between 50° C. and 60° C.

Many of the examples which follow require the reaction of a compound with basic nitrogen containing group and a carboxylic acid. The products of this type of reaction are the ammonium ion of the compound containing the nitrogen atom and the carboxylate anion of the carboxylic acid employed and water. One mole of each reaction product will form when 1 mole of the basic nitrogen containing group is reacted with 1 mole of an acid.

When an excess of the compound containing the nitrogen atom is present the mixture will have an excess of this nitrogen containing compound remaining. That excess is referred to as an un-reacted nitrogen containing compound. Inherent ionization reactions of the basic nitrogen containing group are not included when calculating the molar compositions of the reaction products.

Example 1

A buffered mixture was prepared by reacting 201.0 grams of a 85% aqueous MEA solution (2.80 mol MEA, 1.67 mol water) with 182.8 grams of glacial acetic acid (3.04 mol) and allowing the reaction mixture to cool. The final pH of the mixture was 7.0. The final buffered mixture contained 0.24 moles of acetic acid (un-reacted) and 2.80 moles of the acetate ion, 2.80 moles of the ammonium ion of MEA and 4.47 moles of water.

The buffered mixture was able to dissolve 20% NBPT; however, the material turned yellow over time and emitted an odor of hydrogen sulfide. The yellowing and hydrogen sulfide odor indicated decomposition of NBPT had occurred.

As another example of the instability of this formulation, the buffered NBPT containing mixture was added to ARBORITRE® Binder 75 which is an ethanolamine borate containing copper (II) ions at about 0.75%. The mixture of the two materials immediately turned brown indicating the presence of sulfides of copper (II).

Example 2

A coated granular urea product containing NBPT was prepared from the buffered solvent comprised of MEA and acetic acid of example 1. The two step process began by melting 10.0 grams of NBPT into 90.0 grams of the freshly prepared buffered mixture with a pH of 7 of example 1 to achieve a solution with 10% NBPT. The second step involved forming the coated product by adding 2.75 g of the buffered solution containing 10% NBPT to 500.0 grams of granular urea and the combined ingredients were mixed to distribute the NBPT over the urea granules. The free flowing final product contained 45.77% nitrogen and 0.055% NBPT.

It was discovered that only freshly prepared solutions of NBPT using the buffered mixture of example 1 could be used for coating urea as the NBPT containing solution caused hydrolysis of the NBPT and released sulfides.

Example 3

A buffered mixture was prepared by reacting 100.0 grams of 85% aqueous MEA (1.64 mol MEA, 0.832 mol water), with 66.6 grams of glacial acetic acid (1.11 mol) and allowing the reaction mixture to cool. The final pH of the mixture was 9.2. The final buffered mixture contained 1.11 mol of the ammonium ion of MEA, 1.11 mol of acetate ion, 1.94 mol of water and 0.53 mol of un-reacted MEA.

The buffered mixture was able to dissolve 12% NBPT. The buffered mixture containing 12% NBPT showed signs of slight crystallization when chilled; however, no signs of yellowing were observed indicating no decomposition of NBPT was occurring.

Example 4

A 10% solution of NBPT in the buffered mixture of example 3 was prepared by melting 20.0 grams of NBPT into 180 g of the buffered mixture of example 3 at 50° C.

Example 5

The buffered mixture of example 4 was used to prepare a liquid fertilizer composition by adding 1.40 grams of the buffered mixture of example 4 to 40.0 grams of UAN solution (32% N). The final liquid fertilizer contained 0.34% NBPT and 30.9% N.

Example 6

A buffered mixture was prepared by reacting 300.0 grams of TEA (2.01 mol) with 44.7 grams of acetic acid (0.744 mol). The final mixture had a pH of 7.6. The final mixture contained 0.744 mol of the ammonium ion of TEA, 0.744 mol of acetate ions, 0.744 mol water and 1.27 mol of un-reacted TEA.

The buffered mixture was able to hold up to 30% NBPT; however, it displayed a tendency to yellow over time indicating decomposition of the NBPT. When a mixture of the buffered mixture containing 20% NBPT was added to the copper (II) containing mixture ARBORITE® Binder 75 the resulting admixture lost its characteristic blue color and appeared green indicating the presence of sulfides in the buffered mixture at a pH of 7.6.

Example 7

A buffered mixture was prepared by reacting 100.0 grams of TEA (0.670 mol) with 1.65 grams of acetic acid (0.0275 mol). The final mixture had a pH of 8.5 The final mixture contained 0.0275 mol of the ammonium ion of TEA, 0.0275 mol of acetate ion, 0.0275 mol of water and 0.643 mol of un-reacted TEA. The buffered mixture was able to dissolve 30% NBPT.

Example 8

A 30% solution of NBPT in the buffered mixture of example 7 was prepared by melting 30.0 g of NBPT into 70.0 of the buffered mixture of example 7. The melting step was conducted at 50° C.

Example 9

A coated granular urea product was prepared from the 30% NBPT containing solution of example 8 by mixing 1.0 grams of the 30% containing NBPT solution of example 8 with 500.0 grams of urea and mixing the combined ingredients to distribute the NBPT over the urea surface. The final free flowing product contained 45.90% nitrogen and 0.060% NBPT.

Example 10

The buffered mixture of example 8 was diluted by mixing 1.25 g of the 30% NBPT containing solution (example 8) with 12.63 grams of a the buffered mixture of example 7 to reduce the NBPT concentration to 2.7%. The diluted mixture containing 2.7% NBPT was used to prepare the phosphate coated urea of example 11.

Example 11

A phosphate coated urea was prepared by adding 13.88 grams of the diluted buffered mixture of example 10 (2.7% NBPT) to 500.0 grams of urea and mixing in a planetary mixer to distribute the liquid over the granular urea surface. After distribution of the liquid 107.3 grams of powdered monoammonium phosphate (11-52-0) was added and the combined ingredients were mixed to distribute the powder over the granular surface to obtain a free flowing product. The final product contained 39.10% nitrogen, 8.98% P2O5 and contained 0.060% NBPT.

Example 12

A buffered mixture was prepared by reacting 100.0 grams of MIPA (1.33 mol) with 59.7 grams of acetic acid (0.994 mol). The final colorless mixture had a pH of 9.0. The final buffered mixture contained 0.994 mol of the ammonium ion of MFPA, 0.994 mol of acetate ions, 0.994 mol water and 0.337 mol of un-reacted MIPA. The buffered mixture was able to dissolve about 30% NBPT.

Example 13

A 25% NBPT containing solution was prepared from the buffered mixture of example 12 by melting 15.8 grams of NBPT into 47.5 grams of the buffered mixture of example 12. The NBPT containing buffered mixture was then added to ARBORITE® Binder 75. No reaction characteristic of the formation of sulfide salts of copper (II) was observed.

Example 14

The 25% NBPT containing buffered mixture of example 13 was used to prepare a coated urea fertilizer composition. 1 drop of a 1% aqueous mixture of methylene blue was added to 2.00 grams of the mixture of example 13 and then that mixture was added to 500.0 grams of granular urea. The combined ingredients were mixed in a planetary mixture to distribute the liquid over the surface of the granular urea. A free-flowing granular product was obtained with a faint blue color. The granular coated urea product contained 0.10% NBPT, with a nitrogen content of 45.81%.

Example 15

A buffered mixture solution containing 20% NBPT was prepared from the buffered mixture of example 7 comprised of triethanolamine and acetic acid at a pH of 8.5. 20.0 grams of NBPT was melted into 80.0 grams of the buffered mixture of example 7 at 50° C.

Example 16

A liquid fertilizer solution was prepared from the 20% NBPT containing buffered mixture of example 15 by adding 1.50 grams of the buffered mixture of example 15 to 40.0 grams of liquid UAN solution (32% N). The final liquid fertilizer mixture contained 0.72% NBPT and 30.8% N.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A solution for use in reducing the volatility of urea fertilizers comprising N-(n-butyl)-thiophosphoric triamide (NBPT) dissolved in a buffered reaction mixture of an amino alcohol having the formula 1—$(H)_x$—N—$((CH_2)_m$—$OH)_n$ where m is 1-3, x is 0 or 1, and n is 2 when x is 1 and 3 when x is 0 or the formula 2—$(H)_y$—N—$((CH_2)$—$CHOH$—$CH_3)_z$ such that the length of the carbon chain where the secondary hydroxyl group is located is 3, y is 0 or 1, and z is 2 when y is 1 and 3 when y is 0, and a carboxylic acid having 6 or fewer carbon atoms to form an NBPT solution, said buffered reaction mixture containing the ammonium ion of said amino alcohol, the carboxylate ion of said carboxylic acid, and said amino alcohol, and having a pH of 8 to 10.

2. The solution of claim 1, wherein said amino alcohol is selected from the group consisting of diethanolamine, dipropanolamine, triethanolamine, tripropanolamine, diisopropanolamine, triisopropanolamine, and mixtures thereof.

3. The solution of claim 1, wherein from about 15% to about 30% by weight NBPT is dissolved in said buffered reaction mixture.

4. The solution of claim 1, further including a co-solvent.

5. The solution of claim 4, wherein said co-solvent is ethylene glycol or propylene glycol.

6. The solution of claim 1, wherein said solution is diluted with water.

7. The solution of claim 1, wherein the pH of said buffered reaction mixture is from 9 to 10.

8. The solution of claim 1, wherein said carboxylic acid is selected from the group consisting of acetic acid, propionic acid, butyric acid, valeric acid, caproic acid, and mixtures thereof.

9. The solution of claim 1, wherein said amino alcohol has a $pK_a$ of between about 7.5 and 10 and said carboxylic acid has a $pK_a$ of 5 or less.

10. A solution for use in reducing the volatility of urea fertilizers comprising N-(n-butyl)-thiophosphoric triamide (NBPT) dissolved in a buffered reaction mixture of an amino alcohol selected from the group consisting of diethanolamine, dipropanolamine, triethanolamine, tripropanolamine, diisopropanolamine, triisopropanolamine, and mixtures thereof, and a carboxylic acid having 6 or fewer carbon atoms to form an NBPT solution, said buffered reaction mixture containing the ammonium ion of said amino alcohol, the carboxylate ion of said carboxylic acid, and said amino alcohol, and having a pH of 8 to 10.

11. The solution of claim 10, wherein the pH of said buffered reaction mixture is from 9 to 10.

12. The solution of claim 10, further including a co-solvent.

13. The solution of claim 10, wherein said carboxylic acid is selected from the group consisting of acetic acid, propionic acid, butyric acid, valeric acid, caproic acid, and mixtures thereof.

14. The solution of claim 10, wherein said amino alcohol has a $pK_a$ of between about 7.5 and 10 and said acid has a $pK_a$ of 5 or less.

15. A solution for use in reducing the volatility of urea fertilizers comprising N-(n-butyl)-thiophosphoric triamide (NBPT) dissolved in a buffered reaction mixture of an amino alcohol having the formula 1—$(H)_x$—N—$((CH_2)_{m-OH})_n$ where m is 1-3, x is 0 or 1, and n is 2 when x is 1 and 3 when x is 0 or the formula 2—$(H)_y$—N—$((CH_2)$—$CHOH$—$CH_3)_z$ such that the length of the carbon chain where the secondary hydroxyl group is located is 3, y is 0 or 1, and z is 2 when y is 1 and 3 when y is 0, and a carboxylic acid having 6 or fewer carbon atoms selected from the group consisting of acetic acid, propionic acid, butyric acid, valeric acid, caproic acid, and mixtures thereof, to form an NBPT solution, said buffered reaction mixture containing the ammonium ion of said amino alcohol, the carboxylate ion of said carboxylic acid, and said amino alcohol, and having a pH of 8 to 10.

16. The solution of claim 15, wherein the pH of said buffered reaction mixture is from 9 to 10.

17. The solution of claim 15, further including a co-solvent.

18. The solution of claim 15, wherein said amino alcohol has a $pK_a$ of between about 7.5 and 10 and said carboxylic acid has a $pK_a$ of 5 or less.

* * * * *